United States Patent [19]

Sano, deceased et al.

[11] 4,159,271
[45] * Jun. 26, 1979

[54] PROCESS FOR PRODUCING INDOLINE DERIVATIVES

[75] Inventors: Hironobu Sano, deceased, late of Fuji, Japan, by Nobuyuki Sano, legal representative; Sataro Okamura, deceased, late of Shizuoka, Japan, by Eijiro Okamura, legal representative, Kiryu, Japan; Yoshiki Nakayama, Shimizu; Kazunari Hirao, Shizuoka, both of Japan

[73] Assignee: Ihara Chemical Industry Co., Ltd., Tokyo, Japan

[*] Notice: The portion of the term of this patent subsequent to May 2, 1995, has been disclaimed.

[21] Appl. No.: 870,363

[22] Filed: Jan. 18, 1978

[30] Foreign Application Priority Data

Feb. 4, 1977 [JP] Japan ............................ 52-11389

[51] Int. Cl.² ........................................... C07D 209/08
[52] U.S. Cl. ............................................ 260/326.11 R
[58] Field of Search ............................... 260/326.11 R

[56] References Cited

U.S. PATENT DOCUMENTS

| 2,069,662 | 2/1937 | Treppenhauer | 260/326.11 R |
| 3,102,120 | 8/1963 | Breuer et al. | 260/319 |
| 3,117,131 | 1/1964 | Breuer et al. | 260/319 |
| 4,087,442 | 5/1978 | Nakayama et al. | 260/326.11 R |

FOREIGN PATENT DOCUMENTS 1,498,579 1/1978 United Kingdom ........... 260/326.11 R

OTHER PUBLICATIONS

*Indoles, Part One,* Houlihan, ed. Wiley-Interscience, (1972), pp. 462–468.

*Primary Examiner*—Donald G. Daus
*Assistant Examiner*—D. Rivers
*Attorney, Agent, or Firm*—Oblon, Fisher, Spivak, McClelland & Maier

[57] ABSTRACT

Indoline derivatives having the formula

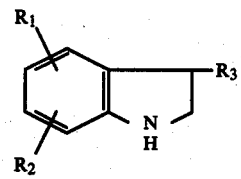

wherein $R_1$, $R_2$ and $R_3$ are defined below are produced by a cyclization of 2-halogenophenethylamine compounds having the formula

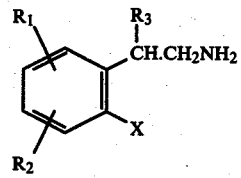

wherein $R_1$ represents hydrogen atom, a lower alkyl, a lower alkoxyl, nitro or hydroxyl group; $R_2$ represents hydrogen atom; a lower alkoxyl or nitro group; $R_3$ represents hydrogen atom or a lower alkyl group and at least one of $R_1$, $R_2$ and $R_3$ is a lower alkyl, a lower alkoxyl or nitro group; and X represents a halogen atom, in the presence of a copper type catalyst and ammonia.

5 Claims, No Drawings

PROCESS FOR PRODUCING INDOLINE DERIVATIVES

BACKGROUND OF THE INVENTION

1. Field of the Invention

The present invention relates to a process for producing indoline derivatives having the formula

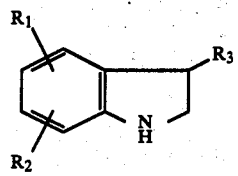

(I)

wherein $R_1$ represents hydrogen atom, a lower alkyl, a lower alkoxyl, nitro or hydroxyl group; $R_2$ represents hydrogen atom, a lower alkoxyl or nitro group; $R_3$ represents hydrogen atom or a lower alkyl group and at least one of $R_1$, $R_2$ and $R_3$ is a lower alkyl, a lower alkoxyl or nitro group; and X represents a halogen atom, which are used as intermediates of indoles which are starting materials for producing agricultural chemicals, medicines, dyes and other industrial products.

2. Description of the Prior Arts

It has been known to produce indoline derivatives by a cyclization of 2-aminophenethyl alcohols having

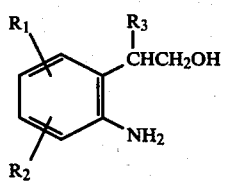

wherein $R_1$, $R_2$ and $R_3$ are defined above in the presence of hydrochloric acid as follows.

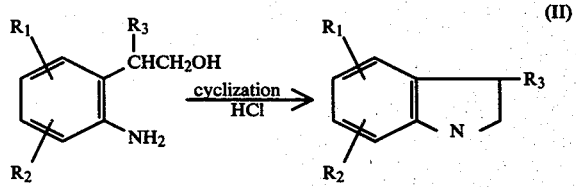

(II)

However, in the method, 2-amino phenethyl alcohols (II) are easily decomposed by heating and by-products of polymers are formed in the reaction whereby, it has been difficult to obtain indoline having high purity in high yield.

SUMMARY OF THE INVENTION

Accordingly, it is an object of the present invention to overcome the disadvantages and to produce indoline derivatives having high purity in high yield.

The object of the invention has been attained by producing indoline by a cyclization of 2-halogenophenethylamine compound having the formula

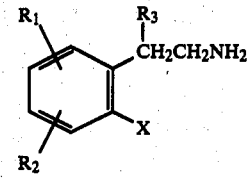

wherein $R_1$ represents hydrogen atom, a lower alkyl, a lower alkoxyl, nitro or hydroxyl groups; $R_2$ represents hydrogen atom, a lower alkoxyl or nitro group; $R_3$ represents hydrogen atom or a lower alkyl group and at least one of $R_1$, $R_2$ and $R_3$ is a lower alkyl, a lower alkoxyl or nitro group; and X represents a halogen atom, in the presence of a copper type catalyst and ammonia.

DETAILED DESCRIPTION OF THE PREFERRED EMBODIMENTS

The reaction of the invention is as follows.

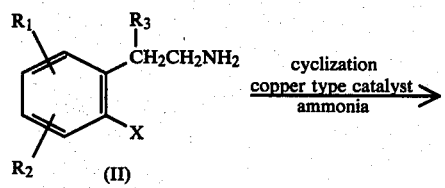

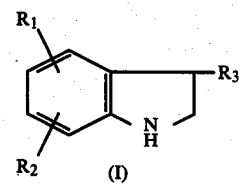

(I)

In 2-halogenophenethylamines (II) used in the present invention, $R_1$ includes hydrogen atom and lower alkyl groups such as methyl, ethyl, n-propyl, i-propyl, n-butyl and i-butyl groups; lower alkoxyl groups such as methoxy, ethoxy, n-propoxy, i-propoxy and n-butoxy groups or nitro or hydroxyl groups which can be bonded at suitable position on the benzene ring; $R_2$ includes hydrogen atom and lower alkoxyl groups such as methoxy, ethoxy, n-propoxy, i-propoxy and n-butoxy groups and nitro group which can be bonded at suitable position on the benzene ring; $R_3$ includes hydrogen atom and lower alkyl groups such as methyl, ethyl, n-propyl, i-propyl, n-butyl and i-butyl groups; and X includes halogen atoms such as fluroine, chlorine, bromine and iodine atoms.

In the practical operations, it is preferable to use as 2-halogenophenethylamines, 2-bromo-$\beta$-methylphenethylamine, 2-chloro-$\beta$-(n-butyl)phenethylamine, 2-chloro-5-(i-propyl)phenethylamine, 2-chloro-4-methyl-$\beta$-(n-butyl)phenethylamine, 2-chloro-4-methoxyphenethylamine, 2-bromo-4-(i-propoxy)phenethylamine, 2-bromo-4-ethoxy-$\beta$-ethylphenethylamine, 2-iodo-4-nitrophenethylamine, 2-fluoro-4-nitro-$\beta$-(i-propyl)-phenethylamine, 2-fluoro-4-hydroxyphenethylamine, 2-chloro-4-hydroxy-$\beta$-ethylphenethylamine, 2-bromo-4-(i-propoxy)-5-(i-propyl)phenethylamine, 2-chloro-4,5-dimethoxyphenethylamine, 2-chloro-4,5-di(i-propoxy)-$\beta$-methylphenethylamine, 2-bromo-5-nitro-4-(i-propoxy)phenethylamine, 2-bromo-5-methoxy-4-nitro-$\beta$-ethyl phenethylamine, 2-chloro-4-hydroxy-5-methoxyphenethylamine, 2-chloro-4-hydroxy-5-(i-propoxy)-$\beta$-(i- propyl)phenethylamine, 2-fluoro-4-methyl-5-nitrophenethylamine, 2-chloro-4-(n-butyl)-5-nitro-β-methylphenethylamine, 2-bromo-3,5-dinitrophenethylamine, 2-bromo-3,5-dinitro-β-ethylphenethylamine, 2-chloro-4-hydroxy-5-nitrophenethylamine and 2-bromo-4-hydroxy-5-nitro-β-ethylphenethylamine.

The catalysts used in the invention can be copper type catalysts to feed copper ions in the reaction system. Suitable catalysts include metallic copper and inorganic copper compounds and copper salts of organic acids, such as cuprous chloride, cupric chloride, cuprous bromide, cupric bromide, cuprous iodide, cupric iodide, cuprous oxide, cupric oxide, cuprous hydroxide, cupric hydroxide, cuprous cyanide, cupric cyanide, cuprous nitrate, cupric nitrate, cuprous sulfate, cupric sulfate, cuprous oxalate, cupric oxalate, cuprous acetate, cupric acetate etc.

An amount of the catalyst is usually 0.1 to 20 wt.% preferably 1 to 5 wt. % as Cu to the starting material of 2-halogenophenethylamine compound (II).

The reaction of the invention is carried out in the presence of ammonia, such as liquid ammonia, ammonia aqueous solution or ammonia-alcohol solution dissolved in an inert solvent.

Suitable inert solvents include water, aliphatic alcohols such as methyl alcohol, ethyl alcohol, i-propyl alcohol and n-butyl alcohol; aromatic hydrocarbons such as benzene, toluene and xylene; ethers such as dioxane, tetrahydrofuran and ethyl ether. It is preferable to use water, methyl alcohol and ethyl alcohol.

An amount of ammonia is 1 to 20 moles preferably 2 to 7 moles per 1 mole of the 2-halogenophenethylamine (II).

The reaction of the present invention is usually carried out in an autoclave by heating the copper type catalyst, ammonia in the form of gas, liquid or a solution dissolved in an inner solvent and 2-halogenophenethylamine compound (II) under stirring.

The reaction temperature is in a range of 80° to 220° C. preferably 120° to 220° C. The pressure in the reaction is considered depending upon the reaction temperature and usually in a range of 5 to 35 Kg/cm$^2$ and the reaction time is in a range of 1 to 6 hours.

After the reaction, the reaction mixture is treated by a filtration or a phase separation, a water washing etc. to separate the copper type catalyst, ammonia and ammonium halides caused by the reaction and then, a distillation or a recrystallization etc. to obtain the indoline derivative (I) in high yield.

The characteristics and advantages of the present invention are as follows.

The characteristics of the present invention are to smoothly perform the cyclization without a formation of a by-product such as polymers in comparison with the cyclization of 2-aminophenethyl alcohols in the presence of hydrochloric acid.

In accordance with the process of the present invention, the indoline derivatives having high purity can be obtained in high yield.

The present invention will be illustrated in detail by certain examples.

EXAMPLE 1

In a 300 ml autoclave, 17.0 g (0.1 mole) of 2-chloro-5-methylphenethylamine, 72.9 g (0.6 mole) of 14% ammonia water and 0.47 g of cuprous chloride (3.0 wt.% to 2-chloro-5-methylphenethylamine) were charged and the autoclave was purged with nitrogen and the reaction of the mixture was carried out at 150° C. for 2 hours. During the reaction, the pressure in the autoclave was maintained to 13 Kg/cm$^2$.

After the reaction, the autoclave was cooled to the room temperature and 100 ml of benzene was added to the reaction mixture and the organic phase was separated and washed with water. The resulting organic phase was concentrated under a reduced pressure to distil off benzene and the concentrated solution was distilled to obtain 5-methyl indoline. The product was analyzed by a gas-chromatography to obtain the result of a purity of 99.6%.

EXAMPLE 2

In the autoclave of Example 1, 29.0 g (0.1 mole) of 2-bromo-3,5-dinitrophenethylamine 102.0 g (0.6 mole) of 10% ammonia-ethyl alcohol solution and 0.58 g of cupric oxide (2.0 wt.% to 2-bromo-3,5-dinitrophenethylamine) were charged and the autoclave was substituted with nitrogen gas and the reaction was carried out at 180° C. for 4 hours under stirring it.

During the reaction, the pressure in the autoclave was maintained to 16 Kg/cm$^2$.

After the reaction, the autoclave was cooled to the room temperature and 150 ml of toluene was added to the reaction mixture and the organic phase was separated and washed with water. The resulting organic phase was concentrated under a reduced pressure to distil off toluene and ethyl alcohol and the resulting crystals were recrystallized to obtain 18.0 g of 5,7-dinitroindoline (m.p. 244.0° to 245.0° C.). The product was analyzed by a gas-chromatography to obtain the result of a purity of 99.4% and a yield of 85.6%.

EXAMPLES 3 TO 14

In accordance with the process of Example 1 except using 0.1 mole of 2-halogenophenethylamines (II) and the copper type catalysts and ammonia shown in Table 1, the indoline derivatives (I) shown in Table 1 were produced. The results are shown in Table 1.

Table 1

| | Starting Material | Reaction | | | | |
|---|---|---|---|---|---|---|
| | 2-halogenophenethylamine (II) | Copper type | Ammonia | Temp. | Autoclave pressure | Time |
| Example | 0.1 mole | catalyst amount | sol. amount | (°C.) | (Kg/cm$^2$) | (hr.) |
| 3 | 2-chloro-5-ethylphenethylamine | CuCl 0.74 g (4%) | 14% aq. sol. 60.7 g (0.5mol) | 150 | 14 | 3 |
| 4 | 2-bromo-5-ethyl-β-ethyl-phenethylamine | metal Cu 0.51 g (2%) | 20% aq. sol. 59.5 g (0.7mol) | 200 | 30 | 1 |
| 5 | 2-bromo-5-n-butylphenethyl-amine | Cu$_2$SO$_4$ 0.77 g (3%) | 10% methanol 34.0 g (0.2mol) | 120 | 10 | 6 |
| 6 | 2-chloro-4-methoxyphenethyl-amine | CuCl 0.56 g (3%) | 10% aq. sol. 102 g (0.6mol) | 150 | 16 | 4 |
| 7 | 2-bromo-5-nitro-4-i-propoxy-phenethylamine | CuOH 1.15 g (4%) | 14% aq. sol. 48.6 g (0.4mol) | 160 | 18 | 3 |

Table 1-continued

| | | | | | | |
|---|---|---|---|---|---|---|
| 8 | 2-chloro-4,5-dimethoxy-phenethylamine | $Cu(OOCCH_3)_2$ 1.08 g (5%) | 10% ethanol 51.0 g (0.3mol) | 140 | 13 | 5 |
| 9 | 2-chloro-4-nitrophenethylamine | $Cu(NO_3)_2$ 0.20 g (1%) | 10% ethanol 102 g (0.6mol) | 140 | 14 | 4 |
| 10 | 2-chloro-4-hydroxyphenethyl-amine | CuCl 0.34 g (2%) | 15% methanol 68 g (0.6mol) | 140 | 15 | 3 |
| 11 | 2-chloro-β-methylphenethyl-amine | CuBr 0.51 g (3%) | 14% aq. sol. 72.9 g (0.6mol) | 130 | 12 | 4 |
| 12 | 2-bromo-β-ethylphenethylamine | $Cu_2O$ 0.68 g (3%) | 20% aq. sol. 51 g (0.6mol) | 120 | 8 | 6 |
| 13 | 2-bromo-β-(i-propyl) phenethylamine | $CuCl_2$ 0.73 g (3%) | 10% methanol 119 g (0.7mol) | 140 | 15 | 5 |
| 14 | 2-chloro-β-(n-butyl) phenethylamine | $Cu(OOC)_2$ 1.06 g (5%) | 14% aq. sol. 72.9 g (0.6mol) | 180 | 25 | 2 |
| Ref. | 2-chlorophenethylamine | — | 14% aq. sol. 72.9 g (0.6 mol) | 150 | 13 | 2 |

Note:
In the columns of copper type catalyst, weight % of 2-halogenophenethylamine is shown in ( ).

| | Indoline derivatives | Yield (%) | Purity (%) | Physical property |
|---|---|---|---|---|
| 3 | 5-ethyl indoline | 86.1 | 99.6 | b.p. 110°–111° C./7mmHg |
| 4 | 3,5-diethyl indoline | 85.7 | 99.3 | b.p. 87°–92° C./3mmHg |
| 5 | 5-n-butyl indoline | 85.3 | 99.5 | b.p. 90°–95° C./5mmHg |
| 6 | 6-methoxy indoline | 88.9 | 99.3 | b.p. 145°–146° C./15mmHg |
| 7 | 5-nitro-6-i-propoxy indoline | 87.0 | 99.5 | m.p. 200°–202° C. |
| 8 | 5,6-dimethoxy indoline | 88.6 | 99.6 | m.p. 108.5° C. |
| 9 | 6-nitro indoline | 83.5 | 99.7 | m.p. 65°–66° C. |
| 10 | 6-hydroxy indoline | 85.0 | 99.5 | m.p. 118°–119° C. |
| 11 | 3-methyl indoline | 87.4 | 99.4 | b.p. 67°–69° C./0.45mmHg |
| 12 | 3-ethyl indoline | 85.0 | 99.5 | b.p. 109°–110° C./7mmHg |
| 13 | 3-(i-propyl) indoline | 83.7 | 99.5 | b.p. 72°–75° C./0.9mmHg |
| 14 | 3-(n-butyl) indoline | 81.0 | 99.4 | b.p. 83°–87° C./3mmHg |
| Ref | indoline | 0 | 0 | — |

What is claimed is:

1. A process for producing an indoline derivative having the formula

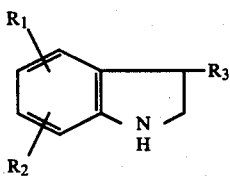

wherein $R_1$ represents hydrogen atom, a lower alkyl, a lower alkoxyl, nitro or hydroxyl group; $R_2$ represents hydrogen atom, a lower alkoxyl or nitro group; $R_3$ represents hydrogen atom or a lower alkyl group and at least one of $R_1$, $R_2$ and $R_3$ is not hydrogen and X represents a halogen atom, which comprises a cyclization of 2-halogenophenethylamine compound having the formula

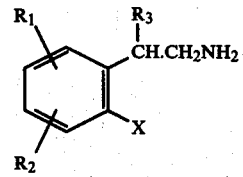

in the presence of copper ions and ammonia.

2. The process of claim 1 wherein said catalyst is combined at a ratio of 0.1 to 20 wt.% as Cu to o-halogenephenethylamine.

3. The process of claim 1 wherein said ammonia is liquid ammonia, ammonia aqueous solution or ammonia alcohol solution and said ammonia is combined at a ratio of 1 to 20 moles per 1 mole of o-halogenephenethylamine.

4. The process of claim 1 wherein said cyclization is carried out at 80° to 220° C. under high pressure of 5 to 35 Kg/cm².

5. The process of claim 1, wherein said ammonia is an aqueous ammonia solution, an ammonia methyl alcohol solution or an ammonia ethyl alcohol solution.

* * * * *